United States Patent
El-Messeiry et al.

(10) Patent No.: US 9,549,867 B1
(45) Date of Patent: Jan. 24, 2017

(54) SEQUENTIAL COMPRESSION DEVICE FOR TREATMENT AND PROPHYLAXIS OF DEEP VEIN THROMBOSES

(71) Applicant: KING SAUD UNIVERSITY, Riyadh (SA)

(72) Inventors: Mamduh A. El-Messeiry, Riyadh (SA); Ali Mohsen Ali Fares Al-Hazmi, Riyadh (SA); Abdulaziz Alhomaidi Alodhayani, Riyadh (SA); Theeb Ayedh Alkahtani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/078,923

(22) Filed: Mar. 23, 2016

(51) Int. Cl.
*A61H 7/00* (2006.01)

(52) U.S. Cl.
CPC .............. *A61H 7/00* (2013.01); *A61H 7/001* (2013.01); *A61H 7/007* (2013.01); *A61H 2201/1207* (2013.01); *A61H 2205/106* (2013.01); *A61H 2209/00* (2013.01)

(58) Field of Classification Search
CPC ............ A61H 7/00; A61H 7/007; A61H 9/00; A61H 9/0007; A61H 9/005; A61H 9/0078; A61H 9/0085; A61H 9/0092; A61H 11/00; A61H 23/00; A61H 23/006; A61H 23/02; A61H 23/0218; A61H 2023/002; A61H 2023/0227; A61H 2209/00; A61H 2205/106; A61H 2205/10
USPC .......... 601/1, 15, 46, 48, 55, 61, 62, 84, 87, 88,601/93, 96, 101, 107, 108, 148, 149, 150, 151,601/152
See application file for complete search history.

(56) References Cited

U.S. PATENT DOCUMENTS

| 8,388,557 B2* | 3/2013 | Moomiaie-Qajar ... A61H 11/00 128/882 |
| 8,755,894 B2 | 6/2014 | Nachum et al. |
| 8,795,210 B2 | 8/2014 | Talish et al. |
| 8,801,576 B1* | 8/2014 | Shin .................. A63B 21/0053 482/1 |
| 9,326,911 B2* | 5/2016 | Wyatt .................. A61H 9/0007 |
| 2005/0159690 A1* | 7/2005 | Barak .................. A61H 9/0078 601/149 |
| 2009/0209900 A1* | 8/2009 | Carmeli ........... A61B 17/22012 604/22 |

(Continued)

FOREIGN PATENT DOCUMENTS

CN 102743277 A 10/2012

*Primary Examiner* — Justine Yu
*Assistant Examiner* — Colin W Stuart
(74) *Attorney, Agent, or Firm* — Richard C. Liman

(57) ABSTRACT

The sequential compression device for treatment and prophylaxis of deep vein thromboses includes a compression sock having a plurality of electromechanical units positioned along the calf muscle of a user's leg. Each of the electromechanical units includes a front housing component and a back housing component. The front housing component of the unit includes a compressor piston positioned in communicating relation with the user's calf muscle and the back housing component of the unit includes a magnet and a copper coil. The magnet is positioned in communicating relation with the compressor piston of the front housing component. Upon activation, the compressor piston selectively compresses the small saphenous vein to simulate the effect of the calf muscle during walking and promote the flow of blood back to the user's heart.

10 Claims, 6 Drawing Sheets

(56) References Cited

U.S. PATENT DOCUMENTS

| | | | |
|---|---|---|---|
| 2012/0259255 A1* | 10/2012 | Tomlinson | A61H 3/00 601/46 |
| 2014/0213940 A1 | 7/2014 | Mayer | |
| 2014/0276296 A1 | 9/2014 | Mansur, Jr. et al. | |
| 2015/0245976 A1 | 9/2015 | Jackson et al. | |
| 2016/0008609 A1 | 1/2016 | Chen | |

* cited by examiner

Fig. 6

SEQUENTIAL COMPRESSION DEVICE FOR TREATMENT AND PROPHYLAXIS OF DEEP VEIN THROMBOSES

BACKGROUND OF THE INVENTION

1. Field of the Invention

The present invention relates generally to medical devices, and more particularly to a sequential compression device for treatment and prophylaxis of deep vein thromboses (DVT).

2. Description of the Related Art

Deep vein thromboses (DVT) are blood clots that form in a vein deep in the body. Blood clots occur when blood thickens and clumps together. Most deep vein blood clots occur in the lower leg or thigh. The small saphenous vein (SSV) is located in the back of the leg calf. Such symptoms as leg pain, tenderness, edema, or swelling are typically associated with deep vein thromboses (DVT). Many times, deep vein thrombosis occurs for no obvious reason. Common symptoms include pain, swelling, and redness in the leg, arm, or other area. However, the risk of developing DVT is increased in certain circumstances, such as damage to a vein's inner lining, age, a long period of not moving, injury to a deep vein from surgery, pregnancy in the first 6 weeks after giving birth, and blood becoming thicker or more likely to clot than normal.

The goals of DVT treatment are to prevent thrombus growth, relieve symptoms, and to prevent DVT and pulmonary embolism (PE) recurrence. The use of compression stockings is an important adjunct to pharmacological treatment in patients with DVT. Compressions stockings help prevent swelling associated with deep vein thrombosis. These stockings are worn on the leg from the feet to about the level of the knees. This pressure helps reduce the chances that blood will pool and clot.

Although the application of compression stockings can appear simple, it must be considered that inappropriately worn stockings have the potential to cause significant problems. Excess pressure may break the skin, especially in older patients.

Thus, a sequential compression device for treatment and prophylaxis of deep vein thromboses solving the aforementioned problems is desired.

SUMMARY OF THE INVENTION

The sequential compression device for treatment and prophylaxis of deep vein thromboses includes a compression sock having a plurality of electromechanical units positioned along the calf muscle of a user's leg. Each of the electromechanical units includes front and rear housing components. The front housing component of the unit includes a compressor piston positioned in communicating relation with the user's calf muscle, and the rear housing component of the unit includes a magnet and a copper coil. The magnet is positioned in communicating relation with the compressor piston of the front housing component. Upon activation, the compressor piston pulsates against the user's calf to simulate the effect of the calf muscle during walking in order to promote the flow of blood back to the user's heart These and other features of the present invention will become readily apparent upon further review of the following specification and drawings.

BRIEF DESCRIPTION OF THE DRAWINGS

FIG. 6 is a diagram of exemplary electronic sequences for activation of the sequential compression device of FIG. 1A in different modes.

Similar reference characters denote corresponding features consistently throughout the attached drawings.

DETAILED DESCRIPTION OF THE PREFERRED EMBODIMENTS

Figure 1A:
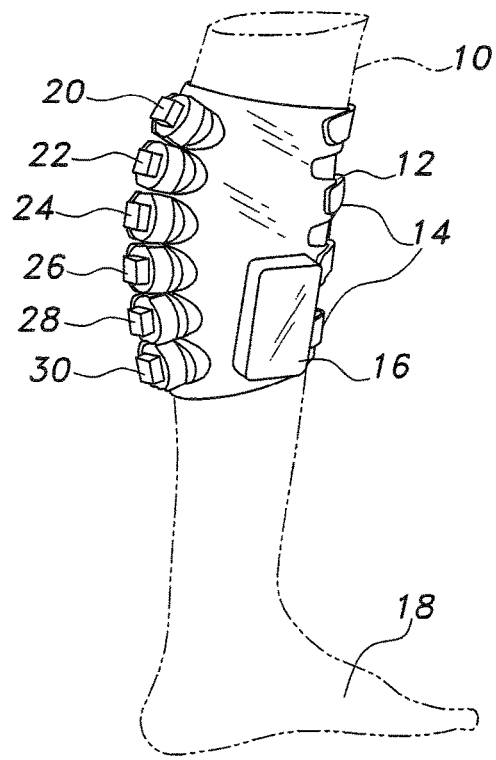
FIG. 1A is an environmental perspective view of an embodiment of a sequential compression device for treatment and prophylaxis of deep vein thromboses according to the present invention.
Figure 1B:
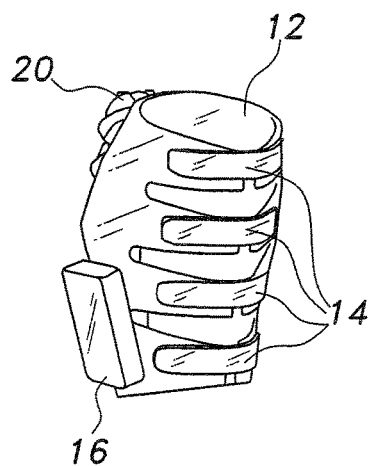
FIG. 1B is a perspective view of the sequential compression device of FIG. 1A.

The sequential compression device for treatment and prophylaxis of deep vein thromboses is a stocking 12 worn on the leg 10 from the feet 18 to about knee level. The device generates sequential pressure only over the SSV vein (small saphenous vein) through six electromechanical units 20, 22, 24, 26, 28, 30 allocated over the SSV vein that simulate the effect of the calf muscle during walking. The units 20, 22, 24, 26, 28, 30 provide a gentle sequential compression to promote the flow of blood back to the heart. These units 20, 22, 24, 26, 28, 30 are wired to the control panel 16. The control panel 16 is attached to lateral side of the device 12 and houses the power supply batteries. The stocking is connected to the leg via belts 14 including mounting fasteners.

Figure 2:
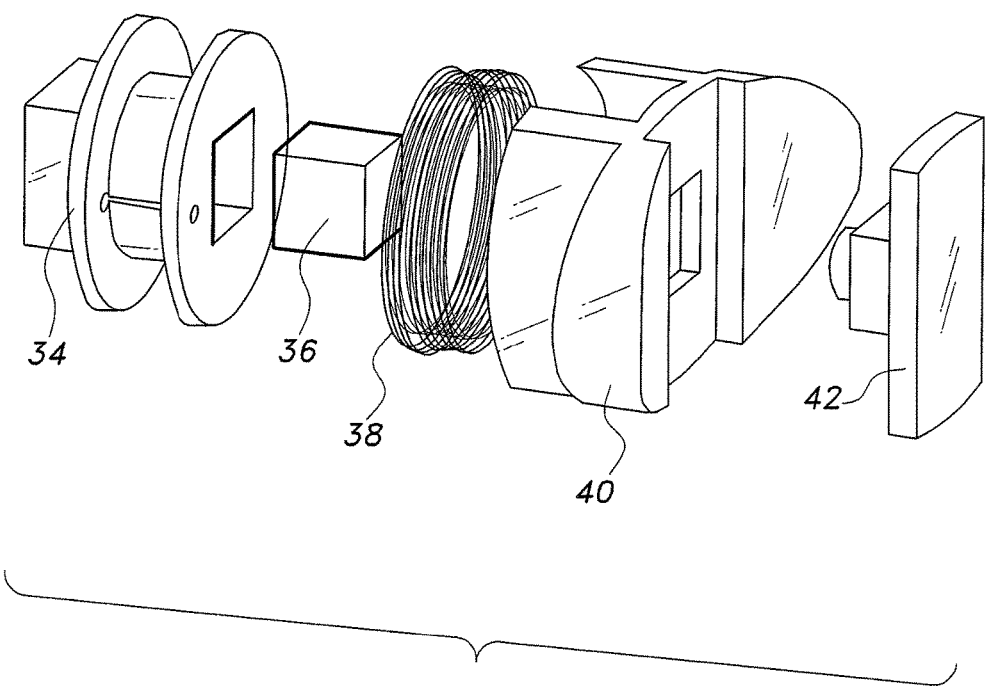
FIG. 2 is an exploded perspective view of an exemplary electromechanical unit in the sequential compression device of FIG. 1A.
Figure 3A:
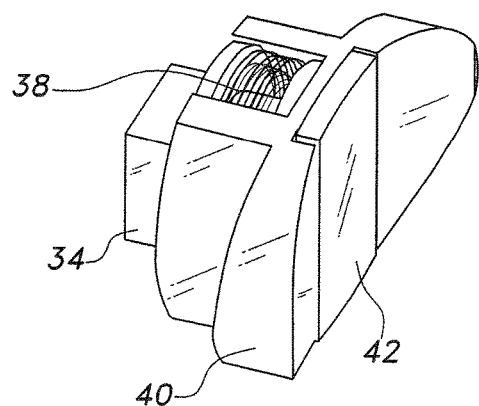
FIG. 3A is a perspective view of an exemplary assembled electromechanical unit of FIG. 2, shown at rest.
Figure 3B:
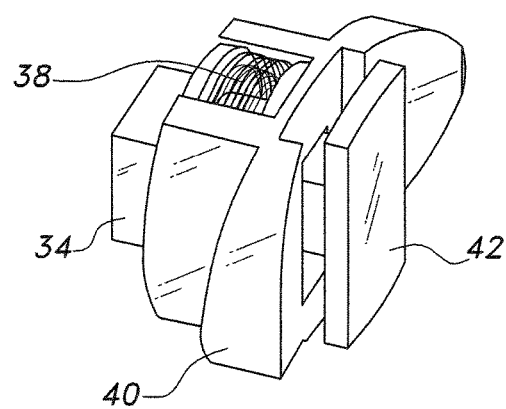
FIG. 3B is a perspective view of the electromechanical unit of FIG. 3A, shown when activated.
Figure 4:
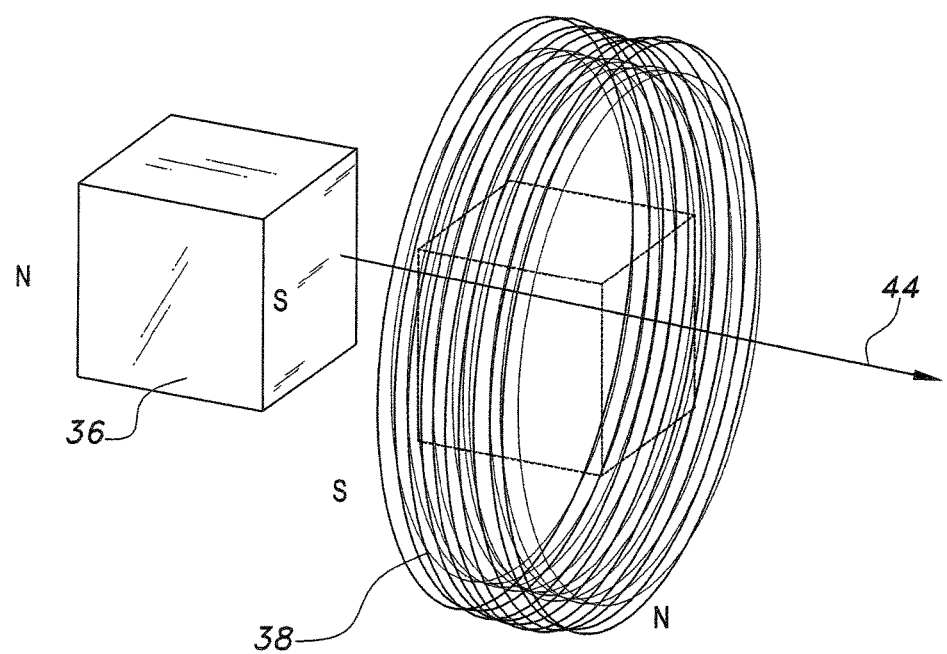
FIG. 4 is a perspective view showing generation of an electromagnetic field in the electromechanical unit of FIG. 2.

As shown in FIG. 2 the electromechanical unit 20, as well as units 22, 24, 26, 28, and 30, includes five pieces. It contains a powerful cuboid magnet 36, which is a Rare Earth Neodymium N35 magnet. It also contains a copper coil 38, which wired to the control panel 16. The coil 38 and the magnet 36 are combined into an assembly in the rear housing component 34. The front housing component 40 contacts the back of the leg calf 10. The curvature of the front housing component 40 fits the curvature of the back of the leg calf. All six electromechanical units 20, 22, 24, 26, 38,-30 are similar in their components, except the curvature of the front housing component 40. The curvature of the front housing component 40 is different in each unit 20, 22, 24, 26, 28, 30 according to the location or elevation of the unit on the back of the leg calf 10. Referring to FIGS. 3A and 3B, the compressor piston 42 extends through a channel in the front housing component 40 and is magnetically attached to the magnet 36. The compressor piston 42 has an elongate polygonal shaft keyed to the channel and a square or rectangular bearing plated centered at one end of the shaft. The compressor piston 42 converts the movement of the magnet 36 when the coil 38 gets electric power. The force and distance that the compressor piston 42 extends out of the channel in the front housing component 40 depends on the voltage and the duration of the electric current that flows in the coil 38. Referring to FIG. 4, the cuboid magnet 36 generates a magnetic field all of the time. The magnet 36 is in a loosened state until the coil 38 generates another magnetic field due to the flow of electric current. At this moment, the southern pole of the magnet 36 is attracted to the northern pole of the coil 38. At the same time, the northern pole of the magnet 36 is also attracted to the southern pole of the coil 38. The magnet 36 will be forced to occupy a new position in the direction 44 and pushes the compressor piston 42 out of the front housing component 40.

Figure 5:
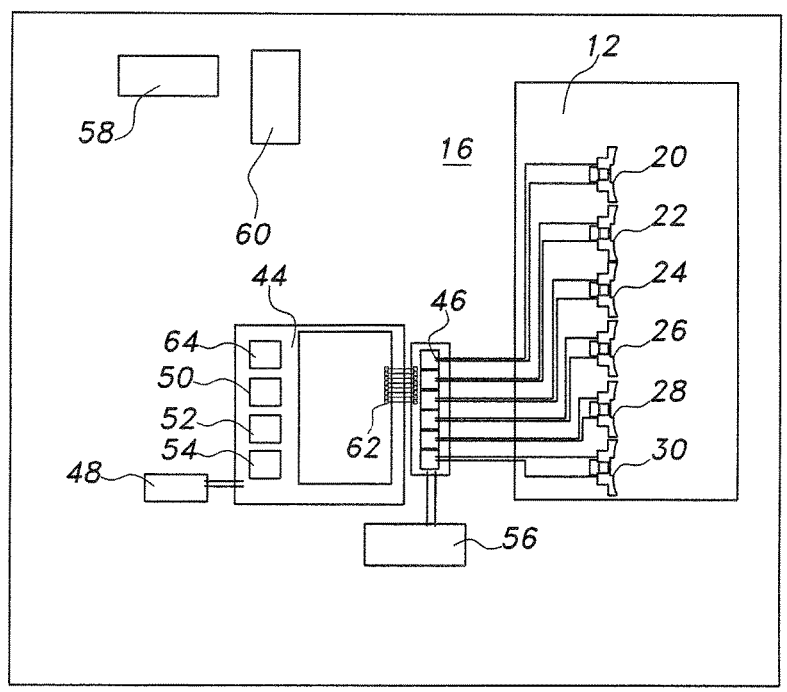
FIG. 5 is a schematic diagram of a control panel for the sequential compression device of FIG. 1A.

As shown in FIG. 5, there is a control panel 16. The entire system is preferably low voltage and electrically powered, having a microcontroller board 44 and operating battery 56, e.g., a 3.7V battery, which is connected to module 46. Module 46 is a six-channel relay module shield. Each channel is wired to the coil 38 on of a corresponding electromechanical unit 20, 22, 24, 26, 28, 30. An external battery 58 can be connected to the relay module 46 to provide longer operational time of the device. The microcontroller board 44 holds the controller, which may be provided from any of a number of sources, an Arduino® microcontroller control board being exemplary. The controller output 62 is six pulse width modulation (PWM) signals. Each channel is wired to one module 46. A USB connector 50 connects the control board 44 to computers. An infrared (IR) wireless remote control module 54 connects the control board 44 to an infrared remote control 60. A Bluetooth module 64 may pair the control board 44 to a smart phone. An SD (secure digital) card interface module with SD slot socket 52 saves data and connects to the control board 44. A 12V battery 48 operates the Microcontroller board 44.

Software makes it easy to write code and to upload it to the board 44 through the USB connection 50. Different code, which represents different operational modes, can be saved through the interface module 52. The code environment is written in Java® and based on processing and other open-source software.

With respect to modes of operation, the sequential compression device has two main functions. The first function is to pump the blood in the SSV through a sequential squeezing along the vein, sequentially upward from the feet to about the level of knees. The compressor piston 42 in the electromechanical unit 30 will project and squeeze the vein. This action is accomplished by starting the electric current in the coil 38 at the lowest electromechanical unit 30 in response to the software code programmed into the microcontroller 44, which connects the power from the battery 56 to the relay 46 and to the coil 38. After an interval, the electromechanical unit 30 will release its pressure on the vein, and the magnet 36 will move rearward to release pressure on the vein. And so in sequence, the electromechanical units will compress and release the vein until reaching the upper electromechanical unit 20, and then start another loop of sequential compression.

Figure 6:
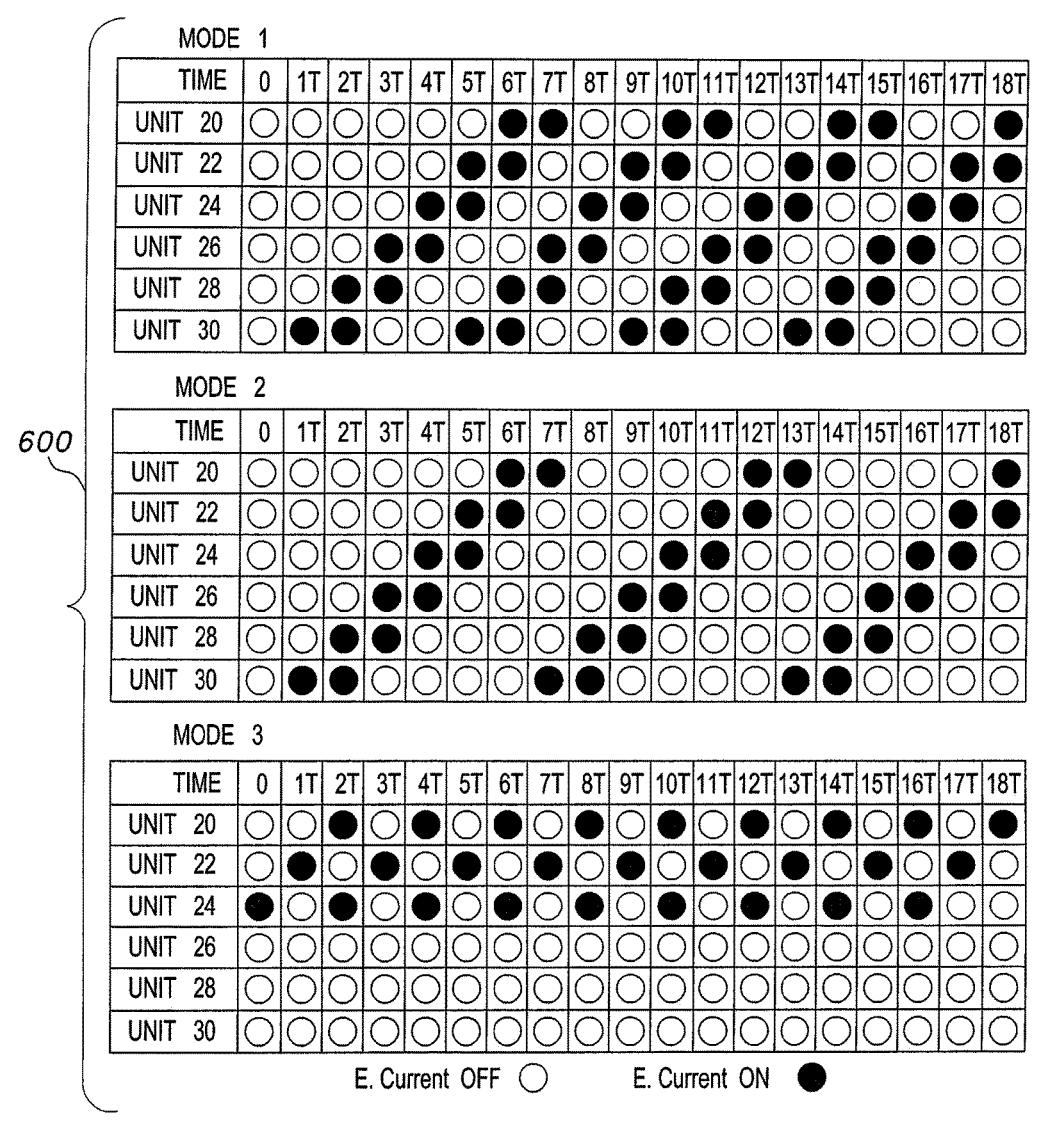

Alternatively, the electromechanically units 20, 22, 24, 26, 28, 30 may be programmed to compress the vein in pairs, as detailed in sequence modes 600 shown in FIG. 6. For example, in Mode 1, in time interval 1T, only unit 30 is activated. Then, in time interval 2T, both units 28 and 30 are activated to apply compression to the vein. In time interval 3T, both units 26 and 28 are activated, while unit 30 is off, the pattern of activation and inactivation continuing as shown in the pattern for Mode 1. Mode 2 is similar to Mode 1, but with the start of the next cycle of compression overlapping the end of the previous cycle.

The software code will control this sequential action and the microcontroller 44 will transfer the code instruction to electric current flow intended time period (T) to the coils 38 in the electro mechanical unit 20-30. The total time to complete one loop or cycle is six times the period (T). Blood flow is high for a small time period (T). Normally, the blood speed in the vein ranges between 5 cm/sec to 15 cm/sec. The calculated time (T) ranges between 0.2 sec and 0.6 sec for a device of length 18 cm.

The value of time (T) is adjusted using the Infrared IR remote control 60 or using a smart phone paired to the Bluetooth module 64. Thereby, the patient can adjust the blood flow in the SSV according to the recommendation of the physician. According to a pilot experiment, Unit 20 is subjected to 3.7 v of electric current; and the maximum force generated was measured as 205 grams, which is enough to compress the SSV. Less compression force can be generated for a patient of low Body Mass Index (BMI) by exchanging the compressor piston 42 with another having a bearing surface of less height.

The second function of the sequential compression device is to massage the SSV. This action can be done by vibrating mode for the upper units 20, 22, 44, for very small period of time (T) that is ranged between 0.05 sec and 0.1. This is shown in Mode 3 of FIG. 6, which shows a different activation pattern, showing unit 24 activated in the first time interval 0, then unit 22 activated in the second time interval 1T, and then an alternating pattern of both units 20 and 24 activated in the next time interval, followed by only unit 22 in the following time interval, an alternating pattern that continues through each cycle of vein compression, thereby massaging the vein.

These modes of operation are stored as software codes on an SD card interface 52, and the patient can control different variables, such as mode of operation and the value of time interval (T), using the Infrared IR remote control 60 or using a smart phone paired to the Bluetooth module 64. The external battery 58 can be wired to the device 12 to provide longer operational time of the device.

It is to be understood that the present invention is not limited to the embodiments described above, but encompasses any and all embodiments within the scope of the following claims.

We claim:

1. A sequential compression device for treatment and prophylaxis of deep vein thromboses, comprising:
   a stocking dimensioned to fit about a patient's calf;
   belts disposed on the stocking;
   mounting fasteners attached to the belts to attach the stocking to the patient's calf;
   a microcontroller;
   a control panel connected to the microcontroller;
   first, second, third, fourth, fifth, and sixth electromechanical units disposed on the stocking and adapted to align with the patient's small saphenous vein in sequential order from upper to lower, wherein each of the electromechanical units consists of:
   i) a front housing component having a curvature adapted for conforming to a back portion of the patient's calf and a channel extending therethrough;
   ii) a back housing component;
   iii) a compressor piston slidably disposed in the channel in the front housing component and adapted to be positioned in communicating relation with the patient's calf muscle;

iv) a magnet disposed in the back housing component, the compressor piston being magnetically attached to the magnet;

v) a copper coil disposed in the back housing component, the copper coil being operably connected to the control panel, whereby a current applied to the copper coil applies a magnetic field to move the magnet and compressor piston so that the compressor piston pulsates against the patient's calf and compresses the patient's small saphenous vein to simulate the effect of the calf muscle during walking to promote flow of blood back to the patient's heart;

a six-channel relay module connected to the first through sixth electromechanical units;

means for energizing the microcontroller, six-channel relay module, and control panel; and wherein the first through sixth electromechanical units are actuated via the six-channel relay module, control panel, and microcontroller to apply sequential compression to a patient's small saphenous vein in a programmable pattern according to a first sequence mode.

2. The sequential compression device according to claim 1, wherein the first sequence mode includes:

activating none of the electromechanical units during a first sequential time period;

activating only the first electromechanical unit during a second sequential time period;

activating only the first and second electromechanical units during a third sequential time period;

activating only the second and third electromechanical units during a fourth sequential time period;

activating only the third and fourth electromechanical units during a fifth sequential time period;

activating only the first, fourth and fifth electromechanical units during a sixth sequential time period;

activating only the first, second, fifth and sixth electromechanical units during a seventh sequential time period;

activating only the second, third and sixth electromechanical units during an eighth sequential time period;

activating only the third and fourth electromechanical units during a ninth sequential time period;

activating only the first, fourth and fifth electromechanical units during a tenth sequential time period;

activating only the first, second, fifth and sixth electromechanical units during an eleventh sequential time period;

activating only the second, third and sixth electromechanical units during a twelfth sequential time period;

activating only the third and fourth electromechanical units during a thirteenth sequential time period;

activating only first, fourth and fifth, electromechanical units during a fourteenth sequential time period;

activating only the first, second, fifth and sixth electromechanical units during a fifteenth sequential time period;

activating only the second, third and sixth electromechanical units during a sixteenth sequential time period;

activating only the third and fourth electromechanical units during a seventeenth sequential time period; and activating only the fourth and fifth electromechanical units during an eighteenth sequential time period.

3. The sequential compression device according to claim 1, wherein the first through sixth electromechanical units are actuated according to a second sequence mode.

4. The sequential compression device according to claim 3, wherein the second sequence mode includes:

activating none of the electromechanical units during a first sequential time period;

activating only the first electromechanical unit during a second sequential time period;

activating only the first and second electromechanical units during a third sequential time period;

activating only the second and third electromechanical units during a fourth sequential time period;

activating only the third and fourth electromechanical units during a fifth sequential time period;

activating only the fourth and fifth electromechanical units during a sixth sequential time period;

activating only the fifth and sixth electromechanical units during a seventh sequential time period;

activating only the first and sixth electromechanical units during an eighth sequential time period;

activating only the first and second electromechanical units during a ninth sequential time period;

activating only the second and third electromechanical units during a tenth sequential time period;

activating only the third and fourth electromechanical units during an eleventh sequential time period;

activating only the fourth and fifth electromechanical units during a twelfth sequential time period;

activating only the fifth and sixth electromechanical units during a thirteenth sequential time period;

activating only the first and sixth electromechanical units during a fourteenth sequential time period;

activating only the first and second electromechanical units during a fifteenth sequential time period;

activating only the second and third electromechanical units during a sixteenth sequential time period;

activating only the third and fourth electromechanical units during a seventeenth sequential time period; and activating only the fourth and fifth electromechanical units during an eighteenth sequential time period.

5. The sequential compression device according to claim 4, wherein the first through sixth electromechanical units are actuated according to a third sequence mode.

6. The sequential compression device according to claim 5, wherein the third sequence mode includes:

activating only the fourth electromechanical unit during a first sequential time period;

activating only the fifth electromechanical unit during a second sequential time period;

activating only the fourth and sixth electromechanical units during a third sequential time period;

activating only the fifth electromechanical units during a fourth sequential time period;

activating only the fourth and sixth electromechanical units during a fifth sequential time period;

activating only the fifth electromechanical units during a sixth sequential time period;

activating only the fourth and sixth electromechanical units during a seventh sequential time period;

activating only the fifth electromechanical unit during an eighth sequential time period;

activating only the fourth and sixth electromechanical units during a ninth sequential time period;

activating only the fifth electromechanical units during a tenth sequential time period;

activating only the fourth and sixth electromechanical units during an eleventh sequential time period;

activating only the fifth electromechanical units during a twelfth sequential time period;

activating only the fourth and sixth electromechanical units during a thirteenth sequential time period;

activating only the fifth electromechanical units during a fourteenth sequential time period;

activating only the fourth and sixth electromechanical units during a fifteenth sequential time period;

activating only the fifth electromechanical unit during a sixteenth sequential time period;

activating only the fourth and sixth electromechanical units during a seventeenth sequential time period; and activating only the fifth electromechanical unit during an eighteenth sequential time period.

7. The sequential compression device according to claim 5, further comprising means for storing the first through third sequence modes as software codes.

8. The sequential compression device according to claim 1, farther comprising means for adjusting an activating time period of the first through sixth electromechanical units during operation of the first sequence mode.

9. The sequential compression device according to claim 1, wherein each magnet is a Rare Earth Neodymium cuboid magnet.

10. The sequential compression device according to claim 1, wherein the front housing component of each said electromechanical unit is different in shape, corresponding with a calf portion that said each electromechanical unit is adapted for conforming to.

* * * * *